United States Patent
Tahmasebi Maraghoosh

(10) Patent No.: US 10,898,162 B2
(45) Date of Patent: Jan. 26, 2021

(54) ULTRASOUND VISUALIZATION OF CURVED STRUCTURES

(71) Applicant: KONINKLIJKE PHILIPS N.V., Eindhoven (NL)

(72) Inventor: Amir Mohammad Tahmasebi Maraghoosh, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 482 days.

(21) Appl. No.: 15/517,218

(22) PCT Filed: Oct. 30, 2015

(86) PCT No.: PCT/IB2015/058395
§ 371 (c)(1),
(2) Date: Apr. 6, 2017

(87) PCT Pub. No.: WO2016/067260
PCT Pub. Date: May 6, 2016

(65) Prior Publication Data
US 2017/0296141 A1 Oct. 19, 2017

Related U.S. Application Data

(60) Provisional application No. 62/072,777, filed on Oct. 30, 2014.

(51) Int. Cl.
*A61B 5/06* (2006.01)
*A61B 8/08* (2006.01)
(Continued)

(52) U.S. Cl.
CPC ............ *A61B 8/0891* (2013.01); *A61B 5/062* (2013.01); *A61B 5/065* (2013.01); *A61B 8/085* (2013.01);
(Continued)

(58) Field of Classification Search
CPC ......... A61B 8/0891; A61B 5/065; A61B 8/54; A61B 8/523; A61B 8/488; A61B 5/062; A61B 8/481; A61B 8/483
See application file for complete search history.

(56) References Cited

U.S. PATENT DOCUMENTS 6,332,089 B1 * 12/2001 Acker ................. A61B 5/0422
128/899
7,772,541 B2   8/2010 Froggatt et al.
(Continued)

FOREIGN PATENT DOCUMENTS

CN        101925333 A     12/2010
CN        102479390 A      5/2012
(Continued)

OTHER PUBLICATIONS

Bühler K et al:"Geometric Methods for Vessel Visualization and Quantification—A Survey", Internet Citation,2002, pp. 1-24Retrieved from the Internet:URL:http://www.vrvis.at/TR/2002/TRVRVis 2002_035_Full.pdf.
(Continued)

*Primary Examiner* — Bill Thomson
*Assistant Examiner* — Amal Aly Farag

(57) ABSTRACT

An ultrasound imaging apparatus may acquire a two-dimensional, flat image of a curved region within a curved plane. The apparatus includes a processor for localizing the region with respect to a transducer array and a processor for operating the transducer array for the imaging of the region and for projecting the region onto a flat image plane. An ultrasound imaging apparatus may acquire a flat image of a curved region within a curved plane. The apparatus may include a module for extracting a centerline of a curved object that contains the curved region, and a processor for: projecting the centerline onto a face of an array, selecting, from among the elements, a set along the projection onto the (Continued)

face, receive beamforming, specifically using the set, to image the curved region and thereby acquire a curved image, and projecting the curved region onto a flat image plane.

12 Claims, 5 Drawing Sheets

(51) Int. Cl.
*A61B 8/00* (2006.01)
*A61B 8/06* (2006.01)

(52) U.S. Cl.
CPC ............ *A61B 8/0841* (2013.01); *A61B 8/481* (2013.01); *A61B 8/483* (2013.01); *A61B 8/488* (2013.01); *A61B 8/523* (2013.01); *A61B 8/54* (2013.01); *A61B 8/06* (2013.01)

(56) References Cited

U.S. PATENT DOCUMENTS

| | | | |
|---|---|---|---|
| 9,017,260 B2 * | 4/2015 | Kanade | A61B 5/06 600/443 |
| 9,384,592 B2 | 7/2016 | Smout et al. | |
| 2009/0079738 A1 * | 3/2009 | Liao | G06T 19/00 345/427 |
| 2010/0214283 A1 | 8/2010 | Lobregt et al. | |
| 2011/0150274 A1 * | 6/2011 | Patwardhan | G06T 7/0012 382/103 |
| 2011/0234780 A1 | 9/2011 | Ito et al. | |
| 2012/0136236 A1 | 5/2012 | Roberts | |
| 2012/0169735 A1 | 7/2012 | Nijlunsing | |
| 2012/0172700 A1 * | 7/2012 | Krishnan | A61B 6/032 600/407 |
| 2013/0009958 A1 | 1/2013 | Kitamura | |
| 2013/0041252 A1 | 2/2013 | Vignon et al. | |
| 2013/0064435 A1 | 3/2013 | Taerum | |
| 2013/0204124 A1 | 8/2013 | Duindam et al. | |
| 2013/0340531 A1 * | 12/2013 | Hutchinson | G01N 29/11 73/633 |
| 2014/0121502 A1 | 5/2014 | Vignon et al. | |
| 2014/0155737 A1 | 6/2014 | Manzke et al. | |
| 2014/0187949 A1 * | 7/2014 | Zhao | A61B 8/12 600/443 |
| 2015/0173707 A1 * | 6/2015 | Ohuchi | A61B 8/0883 345/424 |
| 2015/0173721 A1 | 6/2015 | Satoh et al. | |

FOREIGN PATENT DOCUMENTS

| | | |
|---|---|---|
| JP | 2002315754 A | 10/2002 |
| JP | 2004350791 A | 12/2004 |
| JP | 4109575 B2 | 7/2008 |
| JP | 2012235983 A | 12/2012 |
| JP | 2013192940 A | 9/2013 |
| WO | 2009070616 A2 | 6/2009 |
| WO | 2011102012 A1 | 8/2011 |
| WO | 2012172474 A1 | 12/2012 |
| WO | 2014038703 A1 | 3/2014 |

OTHER PUBLICATIONS

David Williams et al: "Volumetric Curved Planar Reformation for Virtual Endoscopy",IEEE Transactions on Visualization and Computer Graphics, IEEE Service Center,Los Alamitos, CA, US,vol. 14, No. 1,Jan. 1, 2008 (Jan. 1, 2008), pp. 109-119.

Kass et al "Snakes: Active Countour Models" International Journal of Computer Vision, (1988) p. 321-331.

* cited by examiner

ULTRASOUND VISUALIZATION OF CURVED STRUCTURES

This application is the U.S. National Phase application under 35 U.S.C. § 371 of International Application No. PCT/IB2015/058395, filed on Oct. 30, 2015, which claims the benefit of Provisional Application Ser. No. 62/072,777 filed Oct. 30, 2014. These applications are hereby incorporated by reference herein.

FIELD OF THE INVENTION

The present invention relates to imaging a curved region within a curved plane and, more particularly, to imaging a two-dimensional, flat image of the region.

BACKGROUND OF THE INVENTION

U.S. Patent Publication No. 2013/0204124 to Duindam et al. (hereinafter "the '124 publication"), discloses a highly flexible, steerable surgical needle usable for biopsy or other procedures, the needle having a shape sensor. The entire disclosure regarding the shape sensor is incorporated herein by reference. In conjunction with preoperative or intraoperative imaging, output of the sensor can be used in image coregistration. Deviation from a planned needle trajectory can, via the sensor, be detected, and corrected manually or automatically. During insertion, the needle moves generally in a circular path governed by an asymmetric bevel in the needle tip. Rotating the needle shaft, as insertion proceeds, changes the direction of the bevel and thus the path. In addition, unintended deviations of the needle shaft due, for example, to buckling can be tracked.

While the '124 publication tracks sensory data in real time, it is unclear how images are displayed of the curved needle.

SUMMARY OF THE INVENTION

A curved structure, or object, such as a biopsy needle or a vascular structure cannot be visualized in an easy way using conventional display options available on an ultrasound machine. An image plane can be progressively shifted by a few increments in the normal direction to capture the entire structure piecemeal. However, this may distract the clinician or be difficult to perform, and does not include the whole span of the object in a single view of the structure. A three-dimensional rendering does not make clearly visible internally what is in the volume.

In an aspect of what is proposed herein, an ultrasound imaging apparatus is configured for acquiring a two-dimensional, flat image of a curved region within a curved plane. The apparatus includes an ultrasound transducer array for imaging the region. Also included is a localization processor configured for localizing the region with respect to the transducer array. Further included is an ultrasound imaging processor configured for operating the transducer array for the imaging of the region and for projecting the region onto a two-dimensional (2D), flat image plane.

In another aspect, an ultrasound imaging apparatus is configured for acquiring a 2D, flat image of a curved region within a curved plane. The apparatus includes an ultrasound transducer array for imaging the region. The array has a face and transducer elements. The apparatus also includes an image segmentation module configured for extracting a centerline of a curved object that contains the curved region. Further included is an ultrasound imaging processor configured for: projecting the centerline onto the face of the array; selecting, from among the elements, a set along the projection onto the face; receive beamforming, specifically using the set, to image the curved region and thereby acquire a curved image; and projecting the curved region onto a 2D, flat image plane.

Details of the novel, technology for performing, onto a flat plane, a 2D projection of a curved region disposed within a curved plane are set forth further below, with the aid of the following drawings, which are not drawn to scale.

DETAILED DESCRIPTION OF EMBODIMENTS

Figure 1:
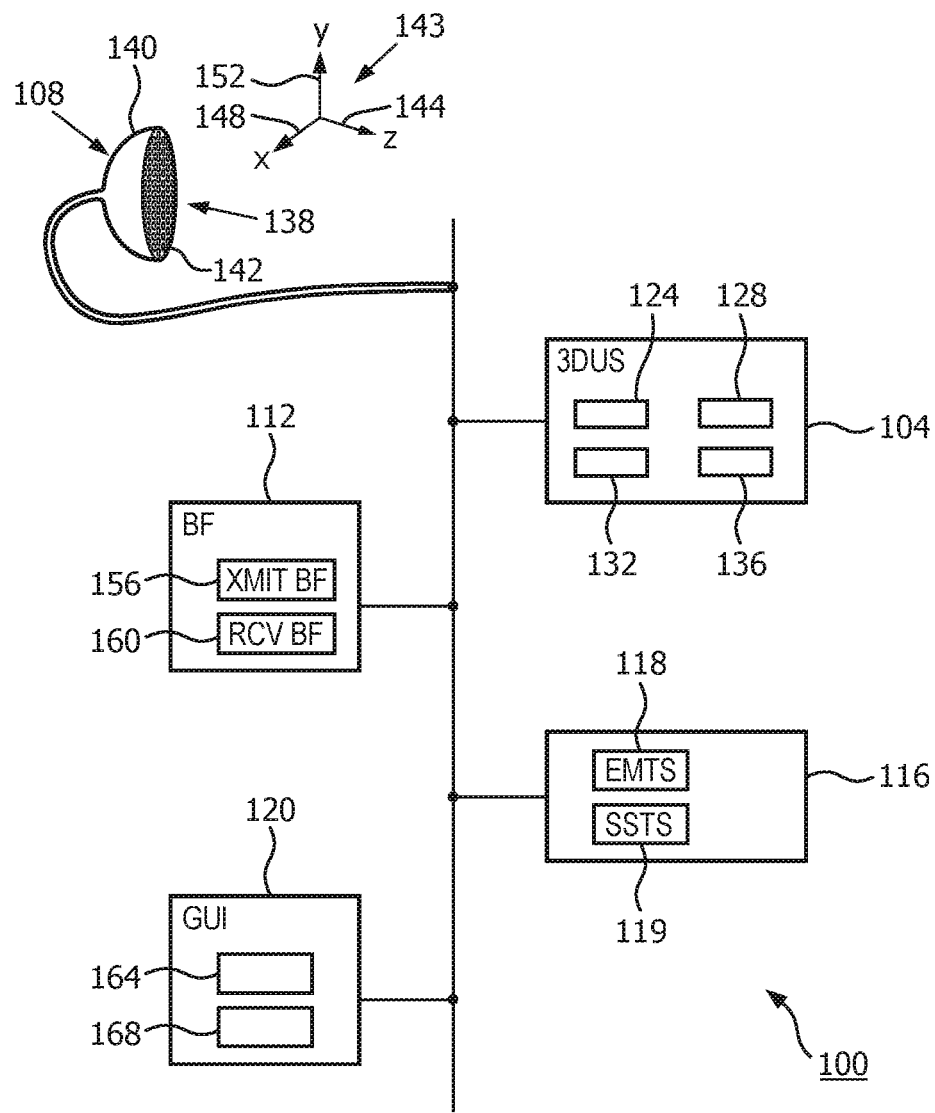
FIG. 1 is a schematic diagram of one example of an apparatus for 2D displaying, onto a flat plane, of a curved region disposed within a curved plane, in accordance with the present invention.

FIG. 1 depicts, by way of illustrative and non-limitative example, an ultrasound apparatus 100 for performing a 2D projection of a curved region disposed within a curved plane. The apparatus 100 includes a 3D ultrasound (US) scanning processor 104, an ultrasound imaging probe 108, an ultrasound beamformer 112, a sensor based localization processor 116, and a graphical user interface (GUI) 120.

The 3DUS scanning processor 104 includes an ultrasound imaging processor 124 and, for image processing based localization, a volumetric imaging localization processor 128, optionally a power Doppler localization processor 132, and an image segmentation module 136.

The imaging probe 108 has an ultrasound transducer array 140 having elements 142, and an acoustic image coordinate frame 143 defined by an axial direction 144, an azimuthal or lateral direction 148, and an elevational direction 152. The array 140 has an ultrasound-communicative face 138 and is configured for acquiring a 3D image, either via a 2D matrix of the elements 142 or, for example, by motorized translation of a 1D array.

The beamformer 112 includes a transmit beamformer 156 and a receive beamformer 160.

The sensor based localization processor 116 includes an electromagnetic tracking system 118 referred to hereinafter as an EMTS, and/or a shape sensor tracking system 119 referred to hereinafter as an SSTS. The EMTS may include in-situ position sensors onboard a curved object, such as a surgical needle or other medical interventional tool, being tracked.

The GUI 120 has 2D display 164, with a 2D display screen, and a user control 168 configured in any known and suitable manner with any one or combination of keyboard, touchscreen, slider, joystick, trackball, etc.

Figure 2:
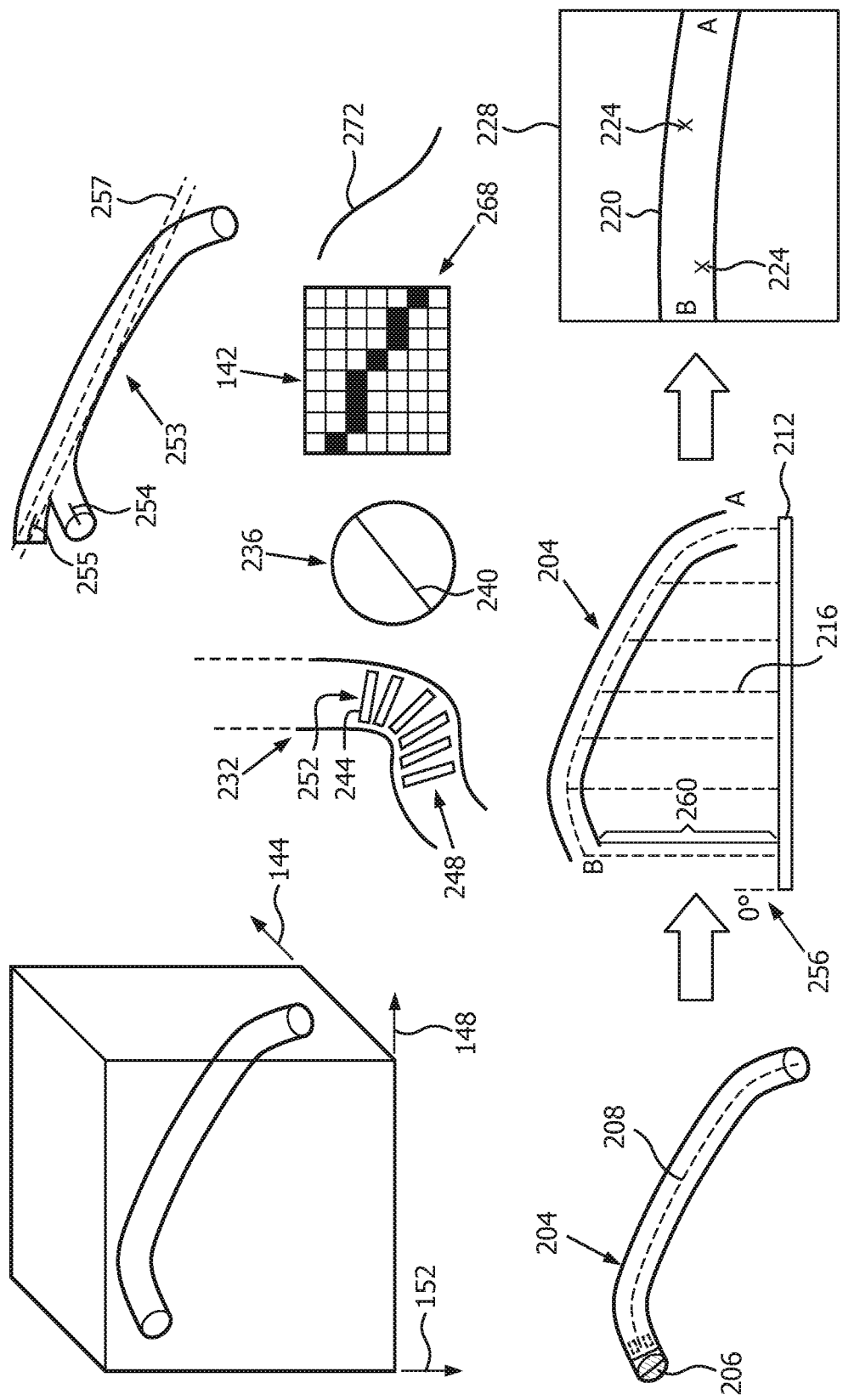
FIG. 2 is a conceptual diagram exemplary of, and pertaining to, the apparatus of FIG. 1.

FIG. 2 portrays acquisition of an image of a curved region and projection onto a flat plane. A curved plane is spatially continuous in two orthogonal directions but deviates from being flat. For example, a tubular object 204 contains a curved region 206, part of which is shown in FIG. 2 with dots to indicate the region continues longitudinally through the object. The tubular object 204 has a centerline, or midline, 208. The curved region 206 contains the centerline 208. A curved plane can be constructed which fully contains the curved region 206 and thus the centerline 208. The tubular object may be elongated, such as in the case of an elongated segment of a blood vessel or curved surgical needle.

The centerline 208 may be projected onto an image plane 212 as indicated in FIG. 2 by lines 216 of projection. An outline 220 of the vessel segment 204 is projected, as are field points 224 aligned with the centerline 208. The field points aligned can make up a generally planar surface which curves with the tubular object 204, and which constitutes the curved region 206. Surrounding anatomy 228 may likewise be projected in alignment with the centerline 208. Here too, the surrounding anatomy field points that are projected may extend the generally planar surface. The centerline 208 and other aligned area of the image, i.e., the extended generally planar surface, make up a two-dimensionally continuous, yet curved, sub-plane within the curved plane. The curved sub-plane, which contains the curved region 206, is projected onto a flat, 2D plane such as the image plane 212 shown in FIG. 2.

The aligned area for a tubular object 232 is formable by taking thin strips that bisect a cross-section 236 of the tubular object. A side view 240 of a thin strip is shown in FIG. 2. The thin strip traverses the interior of the tubular object 232 but, for simplicity of illustration in FIG. 2, its depiction does not extend into walls of the tubular object. The thin strip 244 itself is shown in the alongside perspective view of the tubular object 232. Although there are 360° worth of options on how the thin strip might bisect the cross-section 236, a thin-strip-specific orientation in which the maximum area is projected onto the image plane 212 can be selected. Other strips 248 are constructed for the somewhat twisting tubular object 232. The strips 244, 248 can be made very thin, so as to each correspond to, as well as go through, a respective field point on the centerline 208. Adjacent pairs of the strips 244, 248 may have intervening gaps, due to vessel twisting and directionality changes and due to the angle of view. Optionally, the gaps can be filled by 3D interpolation. In either case, a generally planar surface 252 is available for subsequent projection onto the image plane 212. The generally planar surface 252 can be extended for surrounding anatomy 228. The extended surface is projectable onto the image plane 212 which can then be displayed on the 2D display 164.

For more complex tubular objects, such as a bifurcated vessel segment 253, the bisecting, thin strips may, at a bifurcated portion, extend through respective centerlines 254, 255 of both bifurcated branch portions. The main branch is an elongated curved object containing an elongated curved region 206, and the bifurcating branch is, analogously, a second elongated curved object containing a second elongated curved region.

Although the image plane 212 is shown in FIG. 2 at a particular orientation 256 (i.e., of zero degrees) with respect to the tubular object 204, another orientation may be selected.

An image plane 257 is depicted which, in terms of deviations 260 from the first and second centerlines 254, 255 of the tubular object 264, has an optimal least squares fit to the two centerlines. In the case of a simple vessel segment being examined, an optimal least squares fit can be found to the single centerline 208.

By comparison and by way of example, if the first-mentioned image plane 212 is prepared for the projection by translating the image plane in a normal direction up toward the centerline 204 to minimize the sum of squares of the deviations 260, the orientation 256 of the image plane results in a least squares result that is sub-optimal. Accordingly, the projection may optionally be done, instead, onto the image plane 257 that has been optimally oriented, by a rotation of for example 30 or 36 degrees, so as to achieve an optimal least squares fit.

If, the optimally fitted plane is utilized, the orientation 256 that defines this plane of projection is determined prior to generation of the thin strips 244, 248. Based on a view normal from the optimally fitted plane, the strips can be rotationally oriented about the centerline 208 for maximum projection area onto the plane.

It is noted that that the curved region 206 need not be elongated. A patch of surface coronary tissue, for example, can be volumetrically imaged, localizing the patch to the transducer array 140, and projected onto a pre-designated or optimally fitted imaging plane for display as a B-mode image.

Figure 3:
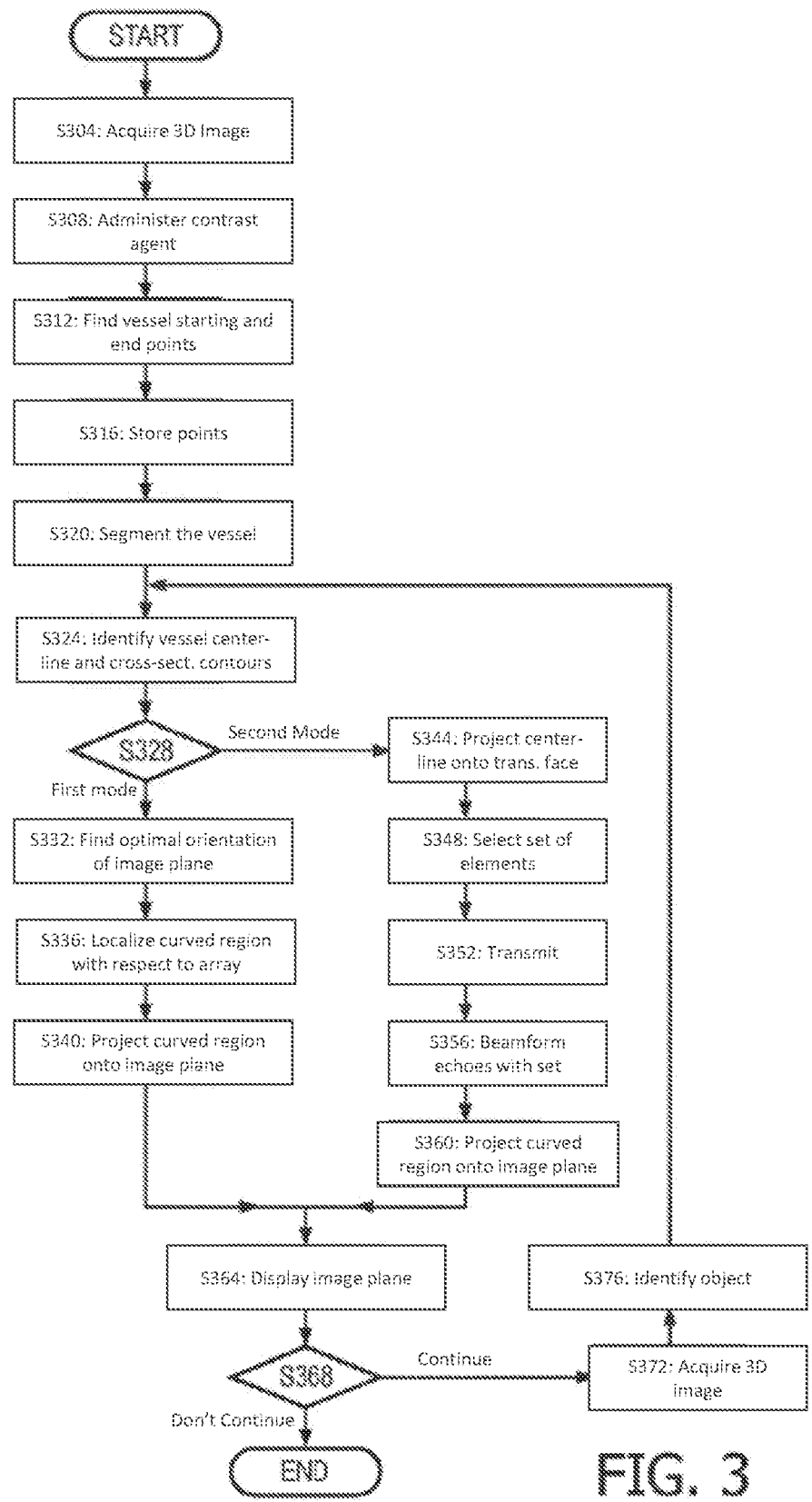
FIG. 3 is a flow chart illustrative and exemplary of 3D volumetric imaging operation according with the present invention.

FIG. 3 is one example of a procedure for imaging a curved region 206, such as in vasculature, that is disposed within a curved plane. A 3D image is acquired (step S304). Ultrasound contrast agent, such as microbubbles, may be administered (step S308). The user, on the GUI 120, scans through B-mode images to find, and interactively indicate, a vessel starting point and a vessel ending point (step S312). The two points might be indicated from different B-mode images. The two points, and an ultrasound image of the delimited vessel segment 204, are stored. Additional points are user-selectable for bifurcated vessel segments 253 (step S316). The vessel segment 204 is segmented, in the imaging sense, by virtue of the delimitation and the contrast agent (step S320). The centerline 208 of the vessel segment 204 and the vessel's cross-sectional contours are identified. The same is performable for the bifurcated vessel segment 253 (step S324). A method for achieving step S324 is disclosed in U.S. Patent Publication No. 2013/0064435 to Taerum (hereinafter "the '435 publication"), from paragraphs [0027]-[0065] the disclosure of which is incorporated herein by reference. A snake, or "active contour", may be used, as in the '435 publication, to determine vessel contours. Two alternative projection modes are available at this point. In a first mode (step S328), a least squares analysis is done to find the optimal orientation 256 of the image plane 257 in fitting it to the centerline(s) 254, 255 (step S332). Alternatively, a specific, predetermined orientation can be designated. The curved region 206 is then determined by the steps discussed herein above and thereby localized with respect to the transducer array 140 or, more specifically, to the acoustic image coordinate frame 143 of the array (step S336). The curved region 206 and optionally its surroundings are then projected onto the designated or optimally fitted image plane 257 (step S340). The surrounding anatomy might not be appended to the curved region 206. For example, the vessel might be imaged in isolation for analysis such as in the '435 publication. Or, for instance, imaging on the optimally oriented image plane 257 might occur interleavingly with the extracted image of merely the curved region 206. If, instead, the other projection mode is chosen (step S328), the centerline 208 is projected onto the ultrasound transducer face 138 (step S344). From among the transducer elements 142, a set 268 is selected along the projection (step S348). The set 268 is elongated, as seen in FIG. 2. It may be given greater width to make the receive beamforming more robust. Transmission, which is not restricted transducer-element-wise, is performed (step S352). The echo is beamformed on receive using the set 268 of transducer elements 142 (step S356). The receive beamforming is performable according to the well-known delay-and-sum technique, the active elements on receive being limited to the set 268. To the extent the centerline 208 is curved in the projection, the image acquired by the receive beamforming will be a "curved" B-mode image plane 272. This curved region, or curved image, is projected onto a 2D flat image plane, as in the other projection mode selectable at step S328 (step S360). For either projection mode, the 2D flat image plane is displayed (step S364). If the displaying is to continue (step S368), a 3D image is acquired (step S372). The object being imaged is identified again in the current 3D acquisition (step S376). This is accomplished by pattern matching, e.g., speckle matching, to the image information stored in step S316. Return is made to the centerline extracting step S324, thereby affording dynamic tracking via live imaging.

Figure 4:
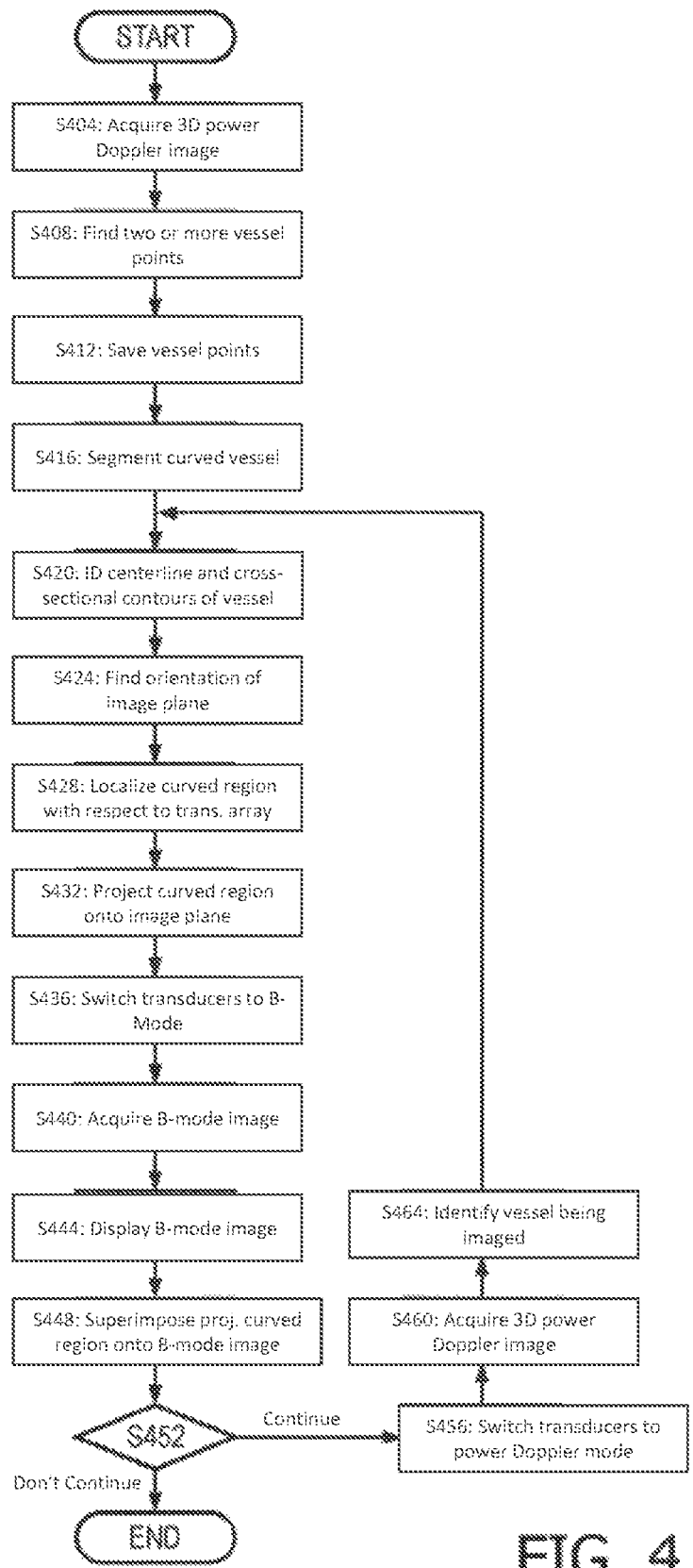
FIG. 4 is a flow chart illustrative and exemplary of power Doppler imaging operation according with the present invention.

An alternative routine for imaging vasculature is presented in FIG. 4. A 3D power Doppler image of the vasculature is acquired (step S404). The user scans through image planes to find two, or more, vessel points that delimit the vasculature to be imaged (step S408). The two, or more, points and an image near the points are saved (step S412). The power Doppler imaging is used to segment the curved blood vessel (step S416). A method as in the '435 publication is utilized to identify the centerline 208 of the vessel segment 204 and the vessel's cross-sectional contours (step S420). The '435 publication mentions use of volumetric pixel intensity values in segmenting a vessel. Power Doppler intensities can serve this purpose. A least squares analysis is done to find the optimal orientation 256 of an image plane 257 in fitting it to the centerline(s) 254, 255 (step S424). Alternatively, a specific, predetermined orientation 256 can be designated. The curved region 206 is then determined by the steps discussed herein above and thereby localized with respect to the transducer array 140, i.e., the acoustic image coordinate frame 143 (step S428). The curved region 206 is then projected onto the designated or optimally fitted, flat image plane (step S432). The transducer elements 142 are switched to B-mode (step S436). A B-mode image is acquired (step S440). The image plane of the B-mode image can be the optimally fitted image plane derived in step S424. The acquired B-mode image is displayed (step S444). The projected curved region 206 is superimposed on the displayed B-mode image (step S448). If processing is to continue (step S452), the transducer elements 142 are switched back to power Doppler mode (step S456). A 3D power Doppler image is acquired (step S460). The vessel being imaged is identified again in the 3D acquisition (step S464). This is accomplished by pattern matching to the image information stored in step S412. Return is made to the centerline extracting step S420.

A straight medical needle is a specular object, and will not reflect ultrasound in a way conducive to good imaging unless the ultrasound beam is approximately normal to the needle. After an initial image, the beam can be steered into a normal direction.

Such a technique is less effective for curved needles.

Figure 5:
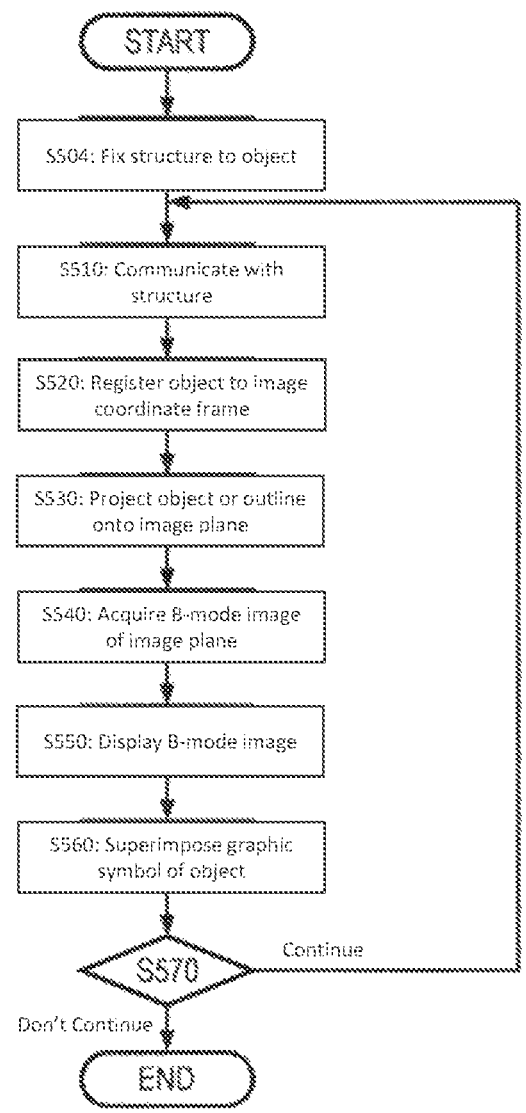
FIG. 5 is a flow chart illustrative and exemplary of 3D sensor/transmitter-based imaging operation according with the present invention.

Referring to FIG. 5, in an exemplary technique for curved objects other than vasculature, such as medical interventional instruments, one or more structures are fixed to the object (step S504). The structures constitute at least one sensor, at least one ultrasound transmitter, or a combination of at least one sensor and at least one ultrasound transmitter. The sensor may be, for example, an EM sensor, a shape sensor, optical sensor, or an ultrasound receiver. Equipping an interventional tool in this manner is described in commonly-assigned U.S. Patent Publication No. 2013/0041252 to Vignon et al., in paragraphs [0003], [0005], and [0075]-[0083] among others. Disclosure on the same topic is found also in commonly assigned U.S. Patent Publication No. 2014/0121502 to Vignon et al., in paragraphs [0075], [0080], [0081], and [0089]. The disclosure in both publications relating to equipping an interventional tool in this manner is incorporated herein by reference. In the case of a single EM sensor onboard the tool, for example, an EM tracking system can be implemented in which both location and orientation information are derived from communication with the onboard sensor. Given a stiff tool, its position and location is then localized. For structures such as ultrasound receivers and ultrasound transmitters whose individual communication, from onboard the object, provides location but not useful orientation information, a plurality of such structures can determine orientation. In the case of a flexible tool, shape sensors are commonly used. An example is the '124 publication mentioned herein above. The entire disclosure including paragraphs [0007]-[0022] and [0045]-[0052], relating to the description herein above, of this publication is incorporated herein by reference. Position and/or shape sensing is also discussed in U.S. Pat. No. 7,772,541 to Froggatt et al. Column 6, line 65 to column 12, line 41 is incorporated herein by reference.

As provided in FIG. 5, the sensor-based localization processor 116 communicates, via the EMTS 118 or SSTS 119, with the one or more sensors or transmitters fixed to the curved object (step S510). The object is registered to the acoustic image coordinate frame 143, and thereby localized (step S520). The registration can occur via a transformation from tracking space to a reference space, and then from the reference space to the acoustic image coordinate frame 143. Or the transformation can be performed directly from the tracking space to the acoustic image coordinate frame 143. The object or its outline is projected onto a flat 2D image plane (step S530). The flat 2D image plane can be pre-designated or optimized in its orientation 256 via a least squares analysis. A B-mode image is acquired of the same image plane (step S540). The B-mode image is displayed (step S550). A graphic symbol depiction of the object, such as spatially its outline, is superimposed for display on the B-mode image (step S560). If displaying is to continue (step S570), return is made to the start of the routine at step S510, thereby providing live imaging for tracking the object.

An ultrasound imaging apparatus is configurable for acquiring a two-dimensional, flat image of a curved region within a curved plane. The apparatus includes a transducer array for imaging the region; a processor for localizing the region with respect to the transducer array; and a processor for operating the transducer array for the imaging of the region and for projecting the region onto a two-dimensional (2D), flat image plane. Alternatively or in addition, an ultrasound imaging apparatus configurable for acquiring a 2D, flat image of a curved region within a curved plane includes a transducer array for imaging the region, the array having a face and transducer elements; a module for extracting a centerline of a curved object that contains the curved region; and a processor for: projecting the centerline onto the face of the array; selecting, from among the elements, a set along the projection onto the face; receive beamforming, specifically using the set, to image the curved region and thereby acquire a curved image; and projecting the curved region onto a 2D, flat image plane.

Although the above discussion is in the context of medical applications, what is proposed herein above is not limited to this area and may, for example, find application in ultrasonic inspection.

While the invention has been illustrated and described in detail in the drawings and foregoing description, such illustration and description are to be considered illustrative or exemplary and not restrictive; the invention is not limited to the disclosed embodiments.

For example, instead of a least squares fit optimization of image plane orientation 256, the criterion could depend on the sum of absolute deviations 260.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The word "exemplary" is used herein to mean "serving as an example, instance or illustration." Any embodiment described as "exemplary" is not necessarily to be construed as preferred or advantageous over other embodiments and/or to exclude the incorporation of features from other embodiments. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache and RAM.

A single processor or other unit may fulfill the functions of several items recited in the claims. The mere fact that certain measures are recited in mutually different dependent claims does not indicate that a combination of these measures cannot be used to advantage.

What is claimed is:

1. An ultrasound imaging apparatus configured for acquiring a flat image of an elongated, curved region disposed within a curved plane, said apparatus comprising:
   an ultrasound transducer array for imaging said curved region that is disposed within said curved plane, wherein the ultrasound transducer array includes a face including a plurality of transducer elements and an acoustic image coordinate frame;
   an image segmentation module configured for segmenting a centerline of an elongated object containing said curved region; and
   an ultrasound imaging processor configured for operating said transducer array for said imaging of said curved region by:
      projecting the centerline onto a plane in the acoustic image coordinate frame corresponding to the face;
      selecting, from among the plurality of transducer elements, a set of transducer elements at a location corresponding to the centerline projected onto the plane;
      receive beamforming, specifically using the set of transducer elements, to image the curved region and thereby acquire a curved image of the curved region; and
      projecting said curved region onto a flat image plane.

2. The apparatus of claim 1, said curved region being a first curved region, one or more second curved regions being elongated and three-dimensional, said imaging processor being further configured for imaging said one or more second curved regions and for projecting said one or more second curved regions onto said flat image plane.

3. The apparatus of claim 2, said imaging processor being configured for, by spatially orienting said flat image plane, fitting said flat image plane to said curved region, and to said one or more second curved regions, in preparation for said projecting of said one or more second curved regions.

4. The apparatus of claim 1, further comprising a user interface, said user interface having a display and a user control, said apparatus being further configured for receiving, via said user control, user input for defining said curved region.

5. The apparatus of claim 4, said imaging processor being configured for said receiving, and for using data received, in said receiving, in deriving a centerline of an elongated object that contains said curved region.

6. The apparatus of claim 4, further configured for, via said display, displaying data outputted by said ultrasound imaging processor, the displayed data depicting said curved region.

7. The apparatus of claim 1, further comprising a display and configured for, via said display, displaying said flat image plane.

8. The apparatus of claim 7, further configured for to dynamically track said elongated object, wherein displaying displays said object as a live image.

9. The apparatus of claim 1, said region being an object, said apparatus being configured for communicating with one or more structures fixed to said object, said one or more constituting at least one sensor, at least one ultrasound transmitter, or a combination of at least one sensor and at least one ultrasound transmitter.

10. An ultrasound imaging apparatus configured for acquiring a flat image of a curved region that is disposed within a curved plane, said apparatus comprising:
    an ultrasound transducer array for imaging said curved region that is disposed within said curved plane, said array having a face and a plurality of transducer elements and an acoustic image coordinate frame;
    an image segmentation module configured for extracting a centerline of a curved object that contains said curved region; and
    an ultrasound imaging processor configured for:
       projecting the centerline onto a plane in the acoustic image coordinate frame corresponding to said face;
       selecting, from among the plurality of transducer elements, a set at a location corresponding to the projection onto said plane;
       receive beamforming, specifically using said set, to image said curved region and thereby acquire a curved image; and
       projecting said curved region onto a flat image plane.

11. A method for acquiring a flat image of a curved region that is disposed within a curved plane, said method comprising:
    segmenting a centerline of an elongated object containing said curved region;
    projecting said centerline onto a plane corresponding to a location of a face of a transducer array in an acoustic image coordinate frame defined by the transducer array, the transducer array including a plurality of transducer elements;
    selecting a set of transducer elements from the plurality of transducer elements at a location corresponding to the centerline projected onto the plane;

receive beamforming using said set of transducer elements to acquire a curved image of the curved region; and projecting said curved region onto a flat image plane.

12. A non-transitory computer-readable medium embodying a program for acquiring a flat image of curved region that is disposed within a curved plane, said program having instructions executable by a processor for performing a plurality of acts, from among said plurality there being the acts of:

projecting said centerline onto a plane corresponding to a location of a face of a transducer array in an acoustic image coordinate frame defined by the transducer array, the transducer array including a plurality of transducer elements;

selecting a set of transducer elements from the plurality of transducer elements at a location corresponding to the centerline projected onto the plane;

receive beamforming using said set of transducer elements to acquire a curved image of the curved region; and projecting said curved region onto a flat image plane.

* * * * *